(12) United States Patent
Xie et al.

(10) Patent No.: US 8,771,275 B2
(45) Date of Patent: Jul. 8, 2014

(54) DEVICE FOR SHAPING OBJECT WITH A PROFILE OF AT LEAST A PARTIAL SPHERE

(76) Inventors: Ping Xie, Ashland, MA (US); Xue Li, Ashland, MA (US)

(*) Notice: Subject to any disclaimer, the term of this patent is extended or adjusted under 35 U.S.C. 154(b) by 568 days.

(21) Appl. No.: 12/236,479

(22) Filed: Sep. 23, 2008

(65) Prior Publication Data
US 2010/0076442 A1   Mar. 25, 2010

(51) Int. Cl.
*A61B 17/00* (2006.01)
*A61B 17/16* (2006.01)

(52) U.S. Cl.
CPC ................................. *A61B 17/1666* (2013.01)
USPC ........................................................... 606/81

(58) Field of Classification Search
USPC ........... 606/80, 81; 30/388–391, 276; 175/96, 175/195, 351, 352, 355, 373, 401, 412, 413, 175/406, 349, 342, 339, 263, 265, 267–273, 175/284, 292; 409/201
See application file for complete search history.

(56) References Cited

U.S. PATENT DOCUMENTS

| | | | | |
|---|---|---|---|---|
| 274,740 A * | 3/1883 | Douglass | ....................... | 175/267 |
| 334,594 A * | 1/1886 | Maloy | ................................. | 125/5 |
| 1,029,491 A * | 6/1912 | Cortinas | ........................ | 175/379 |
| 1,124,241 A * | 1/1915 | Hughes | ........................... | 175/228 |
| 1,131,701 A * | 3/1915 | Hughes | ........................... | 175/339 |
| 1,143,274 A * | 6/1915 | Hughes | ........................... | 175/227 |
| 1,182,533 A * | 5/1916 | Double | ........................... | 175/339 |
| 1,388,496 A * | 8/1921 | Wadsworth | .................... | 175/318 |
| 1,536,034 A * | 4/1925 | Thomas | ........................... | 175/351 |
| 1,723,381 A * | 8/1929 | Seifert | ............................. | 175/334 |
| 1,972,068 A * | 8/1934 | Gill | .................................. | 175/342 |
| 2,016,068 A * | 10/1935 | Bannister | ........................ | 175/96 |
| 2,095,725 A * | 10/1937 | Whealy | ....................... | 15/104.13 |
| 2,435,192 A * | 2/1948 | Arsneau | ........................... | 30/379 |
| 2,637,529 A * | 5/1953 | Howell | ........................... | 175/308 |
| 2,697,457 A * | 12/1954 | Lawrence | ....................... | 30/388 |
| 2,815,050 A * | 12/1957 | Haug | ............................... | 30/388 |
| 3,075,593 A * | 1/1963 | Holsing | ........................... | 175/383 |
| 3,144,086 A * | 8/1964 | Adams et al. | .................... | 175/96 |
| 3,581,832 A * | 6/1971 | Heermann et al. | ......... | 173/162.2 |
| 4,549,614 A * | 10/1985 | Kaalstad et al. | ............... | 175/339 |
| 4,856,503 A * | 8/1989 | Schelhas | ........................... | 606/80 |
| 5,020,281 A * | 6/1991 | Neff | ................................. | 451/358 |
| 5,147,000 A * | 9/1992 | Kaalstad | ....................... | 175/334 |
| 5,702,478 A * | 12/1997 | Tornier | ..................... | 623/22.24 |
| 5,733,288 A * | 3/1998 | Allen | .............................. | 606/79 |
| 5,755,719 A * | 5/1998 | Frieze et al. | ..................... | 606/81 |
| 5,897,558 A * | 4/1999 | Frieze et al. | ..................... | 606/81 |
| 6,120,507 A * | 9/2000 | Allard et al. | ..................... | 606/80 |
| 6,283,971 B1 * | 9/2001 | Temeles | ........................... | 606/81 |
| 6,517,544 B1 * | 2/2003 | Michelson | ....................... | 606/80 |

(Continued)

*Primary Examiner* — Kevin T Truong
*Assistant Examiner* — Zade Coley (57) ABSTRACT

A device for shaping an object with a profile of at least partial sphere defined by a radius, $R_{sph}$ and a maximum breadth, $D_{max}$ of the sphere comprises at least one featured frame. A cutting element has been substantially positioned on a position located within a circular orbit by the featured frame and shaped with at least a portion of circular cutting edge with a uniform radius, $r_{CE}$, which is able to free spinning-able on its spinning axis while, simultaneously the featured frame revolts on a circular orbit around the polar axis of the spherical object. The circular orbit of each cutting element is defined as a motion track of a circular center of the cutting edge around the polar axis and characterized by a radius, $r_{orb}$, and a tilted angle α, thereof.

19 Claims, 7 Drawing Sheets

(56) References Cited

U.S. PATENT DOCUMENTS

| | | | |
|---|---|---|---|
| 6,589,281 B2 * | 7/2003 | Hyde, Jr. | 623/18.11 |
| 6,918,914 B2 * | 7/2005 | Bauer | 606/81 |
| 6,932,172 B2 * | 8/2005 | Dvorachek | 175/432 |
| 7,011,662 B2 | 3/2006 | Lechot | |
| 7,097,646 B2 | 8/2006 | Schantz | |
| 7,217,272 B2 | 5/2007 | Salyer | |
| 7,220,264 B1 | 5/2007 | Hershberger | |
| 7,278,996 B2 | 10/2007 | Wolford | |
| 7,632,276 B2 * | 12/2009 | Fishbein | 606/80 |
| 7,722,615 B2 * | 5/2010 | Botimer | 606/81 |
| 7,922,720 B2 * | 4/2011 | May et al. | 606/80 |
| 2001/0034526 A1 * | 10/2001 | Kuslich et al. | 606/80 |
| 2002/0095214 A1 * | 7/2002 | Hyde, Jr. | 623/18.12 |
| 2004/0073224 A1 * | 4/2004 | Bauer | 606/81 |
| 2004/0167528 A1 * | 8/2004 | Schantz | 606/81 |
| 2005/0049601 A1 * | 3/2005 | Keller | 606/81 |
| 2006/0025774 A1 * | 2/2006 | Fishbein et al. | 606/81 |
| 2006/0217730 A1 * | 9/2006 | Termanini | 606/81 |
| 2006/0276797 A1 * | 12/2006 | Botimer | 606/81 |
| 2007/0016211 A1 * | 1/2007 | Botimer | 606/81 |
| 2007/0276393 A1 * | 11/2007 | Bonadei | 606/80 |
| 2010/0286697 A1 * | 11/2010 | Petit et al. | 606/81 |

* cited by examiner

DEVICE FOR SHAPING OBJECT WITH A PROFILE OF AT LEAST A PARTIAL SPHERE

FIELD OF THE INVENTION

The invention is especially, but not exclusively, applicable to the field of shaping a plurality of object having a profile of at least partial sphere. The present invention could relate orthopedic reamers and other industrial applicability, or like.

DESCRIPTION OF THE PRIOR ART

The reamers for reshaping bone sockets are used widely in current procedures, such as total hip arthroplasty (THA). The plurality of reamers previously invented in the past mostly has derived from idea of the "convex-concave match" design and could be described as that a fully hemispherical thin wall with a specific radius, on which a few cutting edges are projected and well distributed on the convex surface of the wall, forms a hemispherical "cheese grater". Each cutting edge forms a narrow passage conducting from the exterior hemispherical surface into the internal chamber of the cutting head. In particular, the cutting edges may be distributed along a spiral line toward the direction of the rotational axis in order to cover full spherical surface to be cut. When the hemispherical dome cutter rotates around the polar axis of the socket, it scrapes the bone surface and enlarges the socket until reaching the desired radius and shape.

When the reamer as described above is used to prepare a spherical cavity for hip joint prosthesis, several problems are raised. Firstly, the key issues related to the performance of the reamer are that the sharpness and shape of the cutting edges are good enough to generate a qualified surface and accuracy regardless the linear cutting speed acted on. Secondly, due to the variation in the size of the acetabulum in the hip between patients, a series of the reamer head with various sizes are required in order to closely match dimension of the of acetabulum cup for each particular patient. Thirdly, the preparation procedure for the acetabulum needs the enlarging of the native socket to a precise hemisphere. Such an enlargement process requires wearing off native cartilage and rounding the cavity to the expected size, which is typically done with a set of releasable reamer with increasing sizes. To enlarge the acetabulum to the desired size during the reaming, the smaller reamer head must be first used, then removed from the incision of the patient and detached from the shaft, then the larger reamer head be installed, and reinserted into position for further reaming. This procedure may be repeated several times until the cavity matches the dimension of the prosthetic, causing unnecessary prolonged surgical time.

Regarding to problems, designs of the reamer have been changed slightly over the times, by tweaking its configurations without departing the principle of "convex-concave match". Such minor changes have brought some improvements, but also new problems as a trade off, such as more complicated structures, higher manufacturing costs and increased inconvenience of use. The drawbacks and challenges on this conventional design have been well exposed through practices over the years. The primary concerns of users mainly focus on the two aspects on the preparing a concave hemisphere: the quality of the reamed cavity, and the performance of the reamer.

The quality of the reamed cavity should be taken a look on at least three aspects: the roundness of the cavity, the accuracy of the radius, and the smoothness of the surface reamed. Each one is important in affecting the short and long term stability of the implant in the body. The roundness of the cavity formed should be perfect on all latitudes of the sphere made, in order to satisfy the minimum requirement of 70-85% contact area between surfaces of the cavity reamed and the cup outline in the press-fitting procedure of THA. This requirement takes into account fact that new bone growths cannot bridge large gap distances. The roundness of the cavity made is highly dependent on the configuration and quality of the tool used. More specifically, cutting behaviors of any rotating tool depends upon a distribution of the linear cutting speed along the surface and the sharpness and shape of the cutting elements. However, the linear cutting speed considerably varies with where the cutting edge locates on the sphere, on equator circle of the sphere or near the rotary axis. Therefore, the typical hemispherical dome cutter at a given rotary speed and with certain sharpness will present a broad variation in its linear cutting speed differing from latitude to latitude of the sphere. In principle, such uneven cutting speed will typically generate, more or less, an elliptically-shaped cavity. If the sharpness of the cutting edge is not good enough to overcome hard bone faced at lower linear cutting speed, the cavity reamed would hardly meet the minimum requirement for roundness needed for proper press fitting of the metal cup and as a result, an optimal cup fixation by new growth bone cannot be achieved. Obviously, such larger gaps existed might reduce both the initial and long term stability of implant.

The accuracy of the radius is also an important concern. The quality and behavior of the native bone vary from patient to patient with regard to its hardness and elastic properties. In addition to satisfying the requirement of minimum contact area between prostheses and the cavity reamed, the issue of how to prepare a cavity that guaranties guarantees the stability of the prosthesis sited into the cavity, resulting in an ideal outcome with the press-fitting method during and after its installation, is a significant concern for surgeons. One conventional method of THA used to improve stability is to press-fit a slightly larger cup into a smaller spherical cavity reamed. The match of the two depends upon the precise radius of the cavity reamed, the elastic property of the bone and the size difference between two objects. Ideally the elastic property of a health bone should be able to tolerate a size difference of about 1-2 mm and firmly hold the cup on site after impaction. But the elastic behavior of bone from an ill patient is typically either too rigid or too yielding to control the outcomes of installation, therefore making the tolerance of size difference between two objects more difficult to be estimated during installation and critical for maintaining stability thereafter. Therefore, a reamer with the ability to finely tune its cutting profile or to have smaller increment intervals of radius will be highly desirable in order to compensate the effects from variations of bone quality.

The smoothness of the surface reamed refers to the uniformity of the bone surface. New growth bone on site could lead to the bio-fastening of the artificial cup after surgery, thereby increasing the endurance of the implant on the site. But the new bone growth can only cross certain gap distances to bridge surfaces between bone surface and cup attachments. The bowl-shaped cutting edges with wide opening and varied sharpness and its scattering distribution of the hemispherical dome cutter would be too rough to generate a smooth cutting on the surface. Although the roundness and radius may be acceptable in the macro sense, the distance between the two surfaces in groove area may be still too large to encourage new bone growing into the cup attachment. From the debris collected from many clinical occasions, a relatively larger size and irregular shape of the bone particles was obtained. These irregular particles could be attributed to deeply cut or directly peel off from bone surface by "cheese grater". Ideally the bone surface should be finely scraped by very sharp, fine distributed cutting edges with "pin point" contact fashion to result in maximum smoothness of the resulting surface.

In other words, the failures or side effects resulting from such surgery might most likely attribute to the limitations on tool's functions or flaws of the tool rather than a surgeon's experience or skill.

The performance of the reamer is another important aspect, like as the cutting rate, the stability and the self-centralization ability of the reamer. In practice, the hemispherical dome reamers fail to run on fast cutting rates due to concern about the varying linear speeds along the different latitudes of the sphere, the jagged resistance met, due to occasional deep cutting, and friction heat generated by some blunt or blocked cutting edges lost function. The stability and self centralization ability refers to the wobbling or vibration of the reamer during the reaming process, which could lead to shift the cutter and miscut. Sharpness, contact condition of the cutting elements in terms of contact angle, total contact area and its distribution would be key factors for controlling such cutting behaviors of the reamer. Proper design and right material selection for cutting element would minimize cutting resistance and friction and should significantly avoid most problems met.

Another performance concern is the size of the reamer. The larger size of a full hemispherical cutting element is unavoidable in the traditional reamer since the size of hemispherical dome cutter needs to match one of each cavity sought to be reamed. A smaller sized reamer regardless the size of the target is very desirable for two main reasons: a requirement from the growing use of minimally invasive surgical techniques, MIS of THA, and a concern on the lessening of damaging on around tissue during surgery. To further reduce the size of reamer, a new cutting principle have has to be developed without introducing further side effects or drawbacks.

Convenience of use is another importance on the performance of the reamer. Currently the needs for changing cutting heads during the cavity enlargement procedure is very inconvenient and impractical for MIS, since it is very time consuming, causes more damage, and inefficient on tuning the size reamed. A single piece reamer with the ability to continuous control of reaming size and be suitable for most cavity sizes to be reamed, is most desirable for any THA.

Manufacture and maintenance of the reamer parts are a kind of concerns as well. Currently, even though the structure of hemispherical domed reamer is quite simple, the manufacturing and maintenance of this structure is very complicated and costly. This is due to the complexity and costs of the materials used, the special processing applied during its manufacturing, and the maintenance required for preserving the sharpness of the cutting elements.

From the discussion of the important concerns above, it becomes more and more clear that there is a strong desire for an improved reaming system which can address both the quality concerns of the reaming results and the performance of the reamer itself.

SUMMARY OF THE INVENTION

A reamer disclosed in this invention allows for shaping a concave or like with a profile of at least a partial sphere. A typical application of such a reamer is to prepare a cavity for implanting acetabulum cup during either a minimally invasive procedure or a regular operation of THA.

In general, the reamer comprises: a shaft assembly, at least one cutting element and at least one featured frame which couples with the powered shaft and positions the cutting element on its circular orbit. The cutting element is shaped with at least a portion of a circular cutting edge with uniform radius $r_{CE}$ and is able to spin on a secondary axis and revolve on a circular orbit around a primary axis. The orbit of each specific cutting element is defined by parameters a radius of the circular orbit, $r_{orb}$, and a declined angle $\alpha$ thereof.

An advantage of the present invention is that a reamer is designed under a new cutting principle and has a simple structure and smaller size, which has less insertion profile, is of relatively easy operation and more cost effective to manufacture.

Another advantage of the present invention is a reamer including a cutting element that has a higher sharpness, a rational formation and distribution of the cutting edges for minimizing cutting resistance and friction and being able to implement a high quality of the cavity and meet most expectations as discussed above.

Yet another advantage of the present invention is that according to the new principle of reamer(s), different designs of the reamer could be developed, which are able to handle more complicated situations regarding various bone in surgery.

BRIEF DESCRIPTION OF THE DRAWINGS

The following detailed description is directed to certain specific embodiments of the invention. However, the invention can be embodied in a multitude of different ways or designs as defined and covered by the claims. In this description, reference is made to the drawings wherein like parts are designated with like numerals throughout. Furthermore, embodiments of the invention may include several novel features, no single one of which is solely responsible for its desirable attributes or which is essential to practicing the inventions herein described.

The above-mentioned other features and advantages of this invention, and the manner of attaining them, will become more apparent and the invention will be better understood by reference to the following description of embodiments of the invention taken in conjunction with the accompanying drawings, wherein.

DETAILED DESCRIPTION OF PREFERRED EMBODIMENTS

Figure 1A:
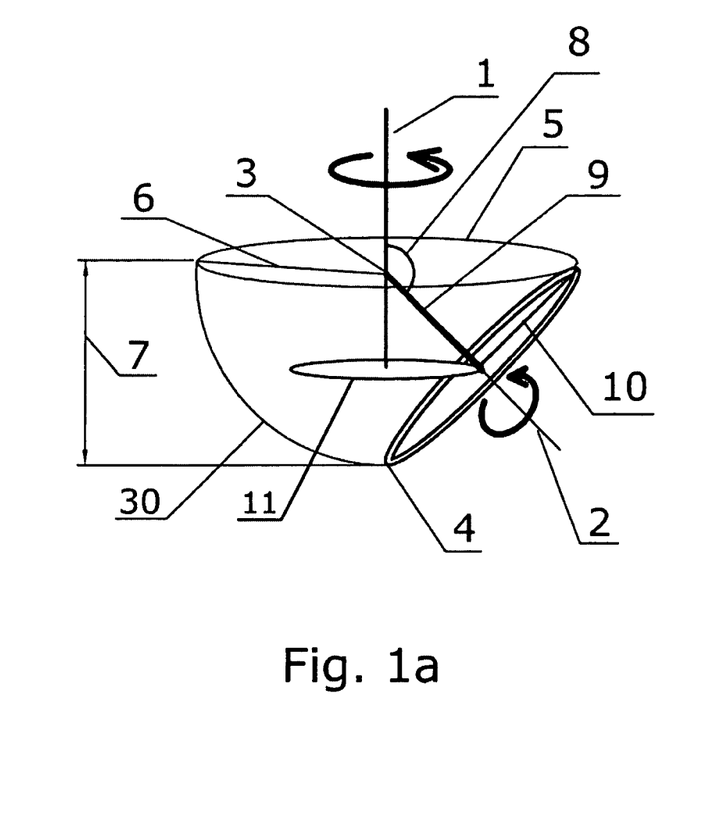
FIG. 1a is a sketch drawing of the geometrical principle followed by the invention and has shown the key corresponding parameters and items used in the detailed descriptions of the invention.

Referring now to the drawings, and more particularly to FIG. 1a, there is a sketch drawing of the geometrical principle of the reamer and defined parameters and definitions used on describing the invention are:

DEFINITION

Primary axis 1: the rotary axis of the reamer and also corresponding to the polar axis of the sphere sought to be cut.

Secondary axis 2: the axis passes through the circular center of the cutting edge and corresponds to the spinning axis of the cutting element.

Virtual center 3 of the reamer assembly or of the featured frame: the intersection point of the primary axis with the secondary axis of each cutting element and also conforms to the center point of the sphere sought to be reamed.

Apex point of reamer assembly 4: the lowest point of the reamer assembly, and equivalent to the polar point of the sphere sought to be reamed.

Equatorial circle 5: the horizontal circle/plane of the reamer assembly with a center at the virtual center and 360 degree around the primary axis.

$R_{sph}$ 6: the radius of the sphere sought to be cut.

Maximum depth of the sphere sought to be cut, $D_{max}$ 7: the vertical distance between the upper and the lower latitude (or point) of the sphere 30 sought to be reamed, which is segmented by cutting elements used (see formula (2) for a precise definition too).

A declined (tilted) angle α 8: the angle between the secondary axis of the specific cutting element and the primary axis of reamer assembly.

Radius of the revolution orbits of each cutting element, $r_{orb}$ 9: the distance between the circular center of the cutting edge and the virtual center of the featured frame or the reamer assembly.

$r_{CE}$ 10: the radius of the circular cutting edge.

The circular orbit of the cutting element 11: the motion track of the circular center of the cutting edge traveled around the primary axis.

Figure 1B:
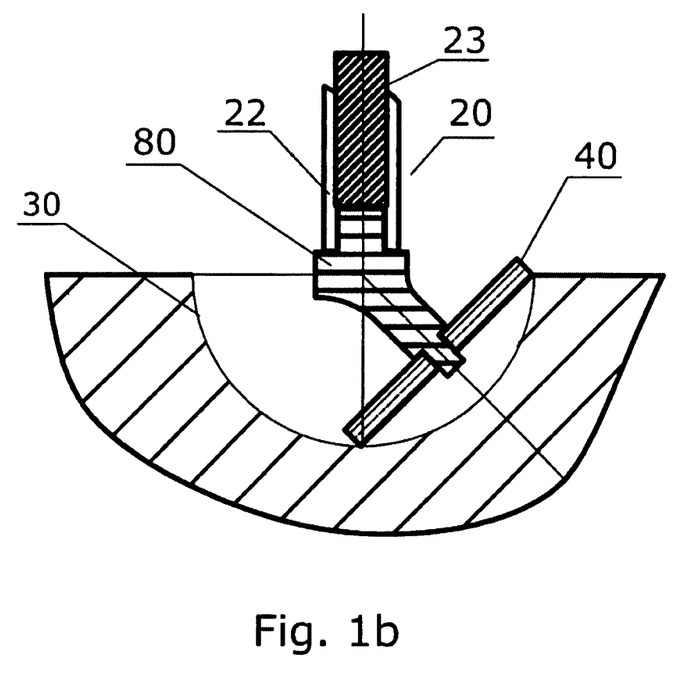
FIG. 1b is a cross-sectional view of the basic structure of a typical reamer assembly deposited in the bone socket to be cut.

As well described in FIGS. 1a and 1b, in general, a reamer substantially comprises 3 components: a shaft of driving mechanism, at least one cutting element(s) 40 and at least one featured frame 80. The featured frame 80 and the cutting element(s) 40 together may construct either an interchangeable reamer assembly or a reamer assembly with adjustable mechanism in order to regulate the cutting profile of the reamer during operation, called "all in one piece" design. A group of the interchangeable reamer assembly configures a series or a set of reamer assembly with incremental radius for enlarging a hemispherical cavity.

The shaft of driving mechanism is rotate-able around the primary axis 1, which is coaxially oriented with the polar axis of the sphere sought to be reamed, and might be comprised of a single shaft 20 or dual shafts, a main shaft 22 and an auxiliary shaft 23, respectively. The dual shafts are concentrically assembled together. The main shaft 22 may be a tubular shaft and be connected to the lower speed end of the transmission by its upper end. The auxiliary shaft 23 may be a rod-like shaft and is concentrically inserted into the inside of the main shaft 22 and connected to the higher speed end of the transmission by its upper end.

The reamer assembly might comprise of one or two featured frame 80. Two featured frame may be assembled on top each other to be able to concentrically rotate on the same rotary axis, the primary axis 1, at different speeds and possess the same virtual center 3. Each featured frame 80 possesses an engagement port or bar for coupling with the corresponding shaft and one or more than one facet site for positioning the corresponding cutting element 40 into its own orbit. Each facet site has been radially extended from the virtual center 3 along the secondary axis 2 of the specific cutting element 40. The configuration of the facet site may be characterized by a radius $r_{orb}$ 9 and a declined angle, α 8 of the orbit 11 for the specific cutting element 40. The parameters for positioning each cutting element 40 in each specific reamer assembly may be predetermined for each interchangeable reamer assembly or be adjustable, if the reamer assembly with the design of the "all in one piece", via a regulating mechanism of the featured frame 80 according to the geometric profile of the sphere sought to be cut.

Each reamer assembly may comprise either one cutting element or more than one piece of the cutting elements. The cutting element 40 may be configured with at least a portion of the circular cutting edge. A typical cutting element 40 for shaping a spherical concave could be either a circular or a half circular cutting blade, with a plurality of the cutting teeth protruding on the circular edge thereof. Each cutting element 40 has a spinning axis through its circular center, called the secondary axis 2, and its own orbit 11 as a traveling track of the circular center thereof revolving around the primary axis 1. The radius, $r_{orb}$ 9 and a declined angle, α 8 also define the characteristics of the orbit of each specific cutting element 40. The cutting element 40 could be either tightly fastened on the lower end of each corresponding facet site or free to spin on each facet site. In addition, the cutting element 40 may also be directly powered by the auxiliary shaft 23 and actively spin on its secondary axis 2, while the featured frame 80 powered by the main shaft 22 has rotated on the primary axis 1. So that the cutting element simultaneously travels and turns along separate rotation axis would eliminate any dead point of cutting at or near the rotation axis. Once the cutting element 40 is positioned into its orbit, the cutting element edges segment the curvature between two latitudes of the sphere sought to be reamed and form chords. Also, the specific curvature of the sphere sought to be cut may be segmented by one or more than one cutting element 40 in many fashions. If segmented by two, either two adjacent or partially overlapped reaming areas would cover the surface of the sphere sought to be cut.

As understood by one skilled in the art, when cutting element 40 assembled has been positioned into the socket to be cut, all cutting teeth on each circular blade are intimately touching or in the approximate area against the bone surface. All cutting teeth could have high sharpness and hardness, due to the better grade of materials chosen, a rational cutting angle toward the surface to be cut, an ideal distribution and formation of teeth, due to more choices on its design and manufacturing method. In addition, there is option on formation and layout pattern for the grooves between adjacent teeth allowing for debris exit. All of them together would optimize the cutting fashion and performances of the reamer.

Like conventional reamer, the device can consist of a series of the interchangeable reamer assemblies with various sizes. Each one is suitable for reaming a cavity with the specific $R_{sph}$ 6 and $D_{max}$ 7. There are three parameters of the reamer assembly for determining its cutting profile as well the geometric profile of the sphere sought to be cut: $r_{orb}$ 9, α 8 and $r_{CE}$ 10, respectively. Only two of them can be varied independently at a time of determining the specific $R_{sp}$ 6 and $D_{max}$ 7. Any two factors or its combination could be selected as adjustable dimensions for tuning an appropriate cutting profile of the reamer assembly into the desired shape. The parameters and their relationship are generally defined by the formula (1) and (2) for a predetermined shape of the cavity. The $R_{sph}$ 6 is satisfied by function of expression as:

$$R_{sph}=\sqrt{(r_{orb})^2+(r_{CE})^2}=\text{square root}((r_{orb})^2+(r_{CE})^2) \quad (1),$$

and the $D_{max}$ 7 generated by function of expression as:

$$D_{max}=2r_{CE}\sin(180-\alpha), \quad (2).$$

Figure 2:
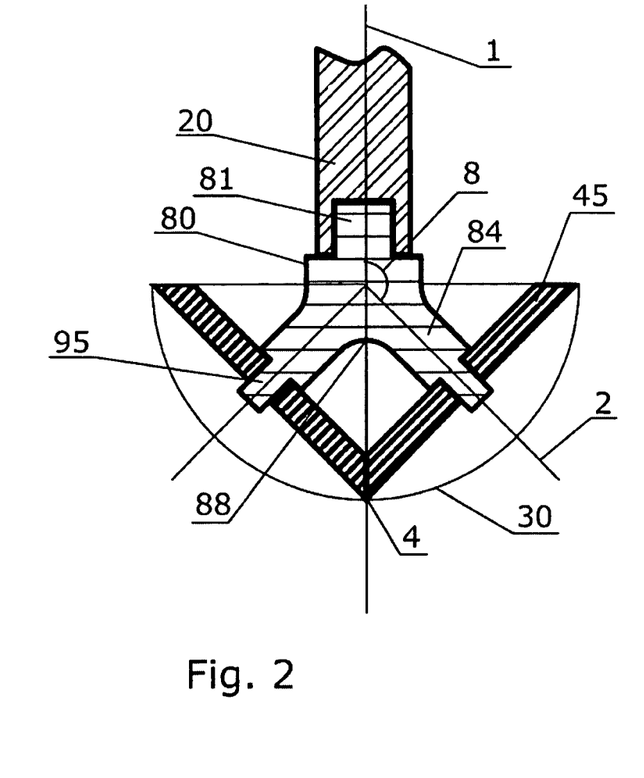
FIG. 2 is a cross-sectional view of an interchangeable reamer assembly with two identical cutting blades symmetrically fabricated on featured frame.

As illustrated in FIG. 2, the first preferred embodiment here describes that the reamer has a single shaft 20 and an interchangeable reamer assembly with two identical cutting elements, such as a circular blade 45 symmetrically fabricated on an featured frame 80 with a respect to the primary axis 1.

The featured frame 80 has equipped an engagement port 81 for coupling with the shaft 20 in any suitable manner, such as threaded engagement, twist and lock, bayonet fittings, etc. The port 81 has a rotary axis coaxially oriented with the primary axis 1 and located on the upper section of the featured frame 80.

There are two identical branched facet sites 84 which are symmetrically split from the virtual center 3 (not shown) of the featured frame 80 with a 90-degree angle 88 therebetween and radially extended along the secondary axis 2. So the configuration of each facet site 84 is characterized by: the declined angle α 8 of the secondary axis 2, which is approximately 135 degree titled from the primary axis 1, and the facet site length, $r_{orb}$, which is the distance between the virtual center and the circular center of the cutting edge and is calculated with formula (1) and (2) discussed above. Or more simply put, the $r_{orb}$ 9 here should be equal to the radii, $r_{CE}$ 10 of the specific blade 45 attached. A spindle 95 shaped for positioning each corresponding cutting blade 45 thereon is located on a distal end of each facet site 84.

Two circular cutting blades 45 are configured with a plurality of cutting edge or teeth have paired and assembled on the spindles 95 properly. As understood by one skilled in the art, the cutting blades 45 could be either tightly fastened on the spindle 95 or be freely spinning on the spindle 95 (on the secondary axis 2). Once assembled, the lower points of two blades would be positioned immediately adjacent each other at or near the apex point 4. Upper points on two blades would meet points on the equatorial circle 5. In other words, the span line of the circular cutting blade would be a chord line that segments the curvature of the hemisphere from the apex point 4 to equatorial circle 5. When the featured frame 80 revolves on the primary axis 1, the lower points of two cutting blades 45 would engage to scrap the apex point 4 of the sphere sought to be cut, the upper points of two cutting blades 45 would engage to ream points on the equatorial circle 5 and cutting teeth projected therebetween would be engaged to scrap points on area of the other remaining latitudes of the sphere. This generates at least a hemispherical surface. Since the cutting blades 45 is passively spun on the secondary axis 2, while simultaneously revolving around the primary axis 1, there are two types of cutting effect acting on the area near apex point 4. In addition, in this configuration, the two cutting blades 45 travel on same orbit track and thoroughly finely cut or scrap each point of surface four times per turn. Therefore, even if various tooth formations protrudes on the circular cutting blades, it would still be able to provide a smooth surface.

A static profile of the reamer assembly presents a V-shaped cross-section instead of the hemispherical one of the dome cutter, as discussed in the prior art. When viewing its dynamic profile of this configuration, while the reamer assembly revolves on the primary axis 1, the profile will appear to be a perfect hemisphere. Obviously, this design has substantially reduced the size of the reamer, which not only provides additional ability for observing the quality and degree of surface reamed in real time, but it also facilitates room of the exclusion of debris during tool operation.

In addition to a full circular cutting blade, cutting elements 40 with the half (or more than half) circular cutting edge could be also adapted into this design of the reamer assembly. Most features remain same as aforementioned above, but the number of the symmetrically extended facet sites 84 on the featured frame 80 could be selected from 2, 3 or 4, corresponding to approximately 180, 120 and 90-degree angle separation between the adjacent facet sites, respectively. The cutting blades would be symmetrically, substantially mounted on the corresponding spindles where the upper point on the cutting edge of each cutting blade 45 merges with point on the equatorial plane 5 and lower points of cutting blade 45 meet at or near apex point 4 of reamer assembly.

Figure 3:
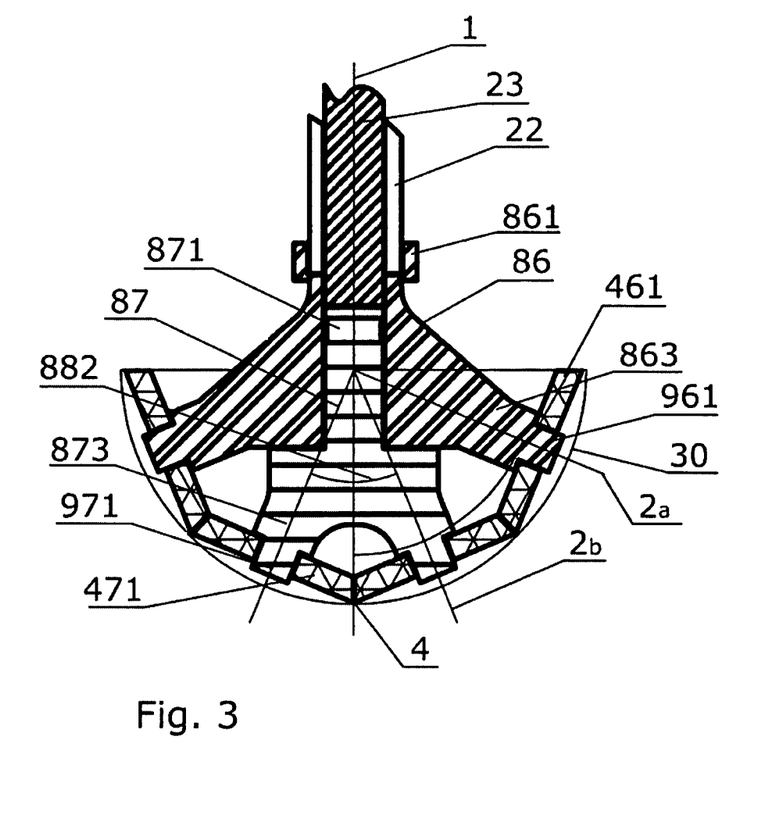
FIG. 3 is a cross-sectional view of other interchangeable reamer assembly with four identical cutting blades fabricated on two levels of featured frame, respectively, in the symmetric arrangement.

As illustrated in FIG. 3, another preferred embodiment describing an interchangeable reamer assembly with four identical cutting elements symmetrically fabricated on two levels of featured frame 86 and 87, respectively with a respect to the primary axis 1 for covering different reaming areas, respectively.

As understanding in description before, the curvature of the sphere 30 could be chorded by more than one adjacent cutting element in different ways. For instance, two adjacent cutting elements with a smaller radius could segment same curvature of sphere 30 described in the first preferred embodiment. More specifically, the radius of each cutting element could be reduced from $1.414R_{sph}$ in the case with one cutting element to $0.653R_{sph}$ in the case with two adjacent cutting elements. This will significantly reduce the profile area from axial view, and subsequently the overall size of reamer assembly.

Furthermore, if the cutting element set with the orbit located on the lower latitude area (near apex point) of the sphere sought to be cut runs at higher rotary speed around the primary axis 1, while the other cutting element set covering the upper latitude area of the sphere runs at relatively lower rotary speed, the reamer would provide a more uniformed cutting rate through entire area than one with a single cutting speed does and further guarantee accuracy of the roundness of the cavity reamed and a higher cutting rate.

More specifically, the upper featured frame 86 and the lower featured frame 87 correspond to ream different latitude areas of the sphere 30 sought to be cut and have the same axis of rotation, the primary axis 1, and the virtual center, but may be powered by the same or separate driving shafts 22 and 23. The lower featured frame 87 is configured with an engagement port 871 that upwardly extends through a center opening of the upper featured frame 86 and is ready to pair with the auxiliary shaft 23 and has two identical facet site 873, which are downwardly extended from the virtual center 3 (no shown). A spindle 971 is deposited on lower distal of each facet site 873 and is coaxially oriented with the secondary axis $2_b$. The secondary axis $2_b$ of two spindles 971 are approximately a 45-degree angle 882 away from each other, which is equivalent to approximately a 157.5-degree tilt from the primary axis 1.

The upper featured frame 86 is concentrically deposited above the lower attachment 87, has a tubular port 861 for connecting with the main shaft 22, which surrounds and concentrically rotates on the outside of auxiliary shaft 23, and has two identical facet sites 863, which are downwardly extended. A spindle 961 on the distal end of each facet site 863 in the upper level extends along the secondary axis $2_a$ that tilted approximately a 112.5-degree angle from the primary axis 1. The two concentrically arranged shafts are driven by motor, but through separated transmission ports and rotate at different rotary speeds. The shaft located in the center, the auxiliary shaft 23, runs at a relatively higher speed rate, which increases the cutting speed of lower cutting blades, compensates the shortage of its smaller rotary radius near apex point 4 and closely matches one driven by the main shaft 22 turning at a regular rotating speed.

The lower points of the two circular cutting blades 471 on the lower featured frame 87 are intimately merged on the apex point 4. The lower points of the two circular cutting blades 461 on upper featured frame 86 are immediately adjacent to the upper points of the two circular cutting blades 471 on the lower featured frame 87. The upper point of two circular cutting blades 461 on upper featured frame 86 is intersected with the points on the equatorial circle 5. The remaining features of elements in this reamer setup are the same as described in the first embodiment. It is important to note that the $r_{orb}$ and $r_{CE}$ of the cutting blade in each level still follow the relationship described in both formula (1), (2), and may be determined by formula (1), (2) according dimension of the sphere sought to be cut.

In comparison with design in first embodiment, the advantages of a two-level set of cutting blades include further reducing the overall size of the reamer and provide a more uniformed cutting speed (rate) of reamer which compensates for the differences in linear cutting speed from variation of rotation radius with the latitude of the sphere reamed. Furthermore, the two sets of cutting blades running at different speed rates would be able to substantially and efficiently centralize and stabilize the reamer in the concave to be reamed. In addition, due to lessened torque felt by the smaller radius of the cutting elements in each level, less power would be needed to power this reamer.

Figure 4:
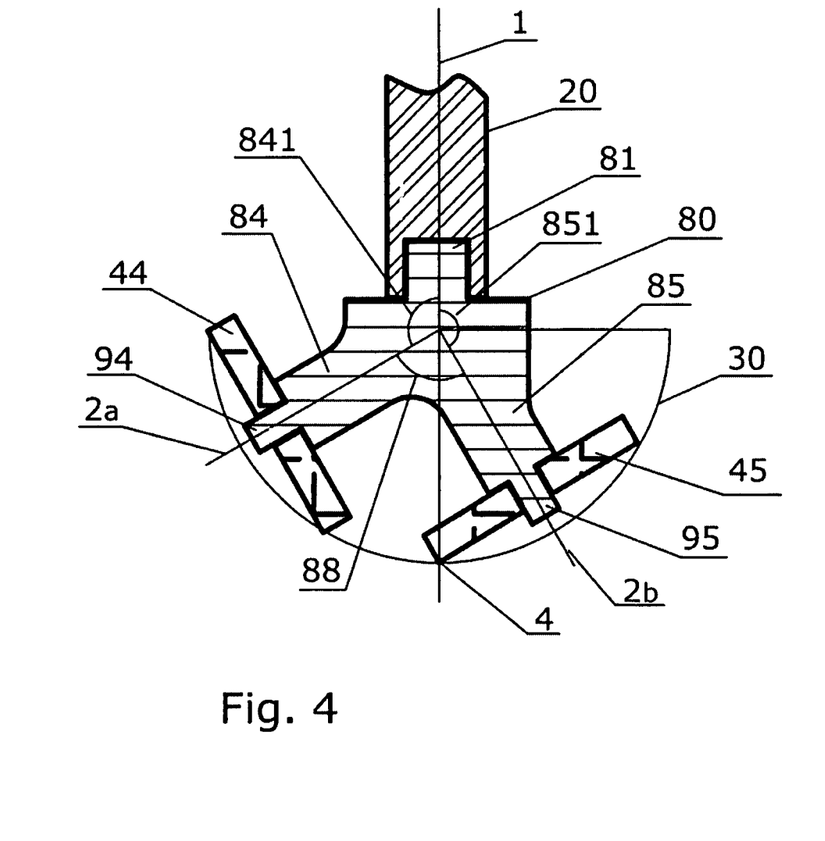
FIG. 4 is a cross-sectional view of another interchangeable reamer assembly with two identical circular cutting blades fabricated on the featured frame in asymmetrical fashion.

As illustrated in FIG. 4, the third preferred embodiment describes that the interchangeable reamer assembly has two identically sized and shaped cutting elements, circular cutting blades 44 and 45, which are asymmetrical situated the featured frame 80 toward the primary axis 1. In this situation, each cutting element assembled would revolve on its own, unique orbit, while around the primary axis 1. The reaming areas corresponding to each orbit may be either immediately adjacent or partially overlapped each other.

More specifically, the featured frame 80 has equipped with an engagement port 81 configured in same manner as described in the first preferred embodiment. Two facet sites 84 and 85 for positioning each specific circular cutting blade 44 or 45 have split from the virtual center of the reamer assembly along their secondary axis $2_a$ and $2_b$, respectively, and radically extended by distance $r_{orb}$ 9. The secondary axis $2_a$ or $2_b$ of each specific facet site may be still branched approximately 90-degree angle 88 away as one described in first preferred embodiment. But facet site one, 84 has tilted $\alpha^1$ 841 degree angle from the primary axis 1 and the facet site two, 85, has tilted an angle, $\alpha^2$ 851 from the primary axis 1. Further more, $\alpha^1 = \alpha^0 - \Delta\alpha$ and $\alpha^2 = \alpha^0 + \Delta\alpha$, respectively. Two circular cutting blades 44 and 45 with identical radius $r_{CE}$ are fabricated on the corresponding spindles 94 and 95 which deposits on the distal end of each facet site 84 or 85. The lower points of the two circular cutting blades 44 and 45 may be apart from each other instead that two are merged together as described in first preferred embodiment. The $\alpha^0$ here has the same definition and the value of $\alpha$ 8 (approximately about 135 degree) as described in first preferred embodiment. But the $\Delta\alpha$ is defined as a swinging or biasing angle of the specific facet site and depends upon size of the sphere sought to be cut, at which the one cutting blade will allows lie on lower orbit and the second cutting blade will lie on the upper orbit. In principle, whilst the lower point of the lower circular cutting blade 45 with appreciate $\alpha^2$ 851 and $r_{orb}^2$ would always deposit on apex point 4 of reamer assembly and the upper point of the upper circular cutting blade 44 with appreciate $\alpha^1$ 841 and $r_{orb}^1$ will intersect with a point on the equatorial circle 5, respectively. The lower and upper orbit correspond to the lower portion and upper reaming area of the curvature reamed, respectively, which may be overlapped each other to a certain extent from case to case.

According to the principle of the design discussed here, the parameter $r_{orb}$ 9 and $\alpha$ 8 are variable as independent factors according to dimension of the sphere sought to be cut. The $r_{CE}$ 10 here is an unchanged factor and would fit into any size of the reamer assembly in series. In other words, as $R_{sph}$ 6 changes from case to case, $r_{orb}$ 9 and $\Delta\alpha$ will be subsequently varied according to formula (1) and (2).

Figure 5:
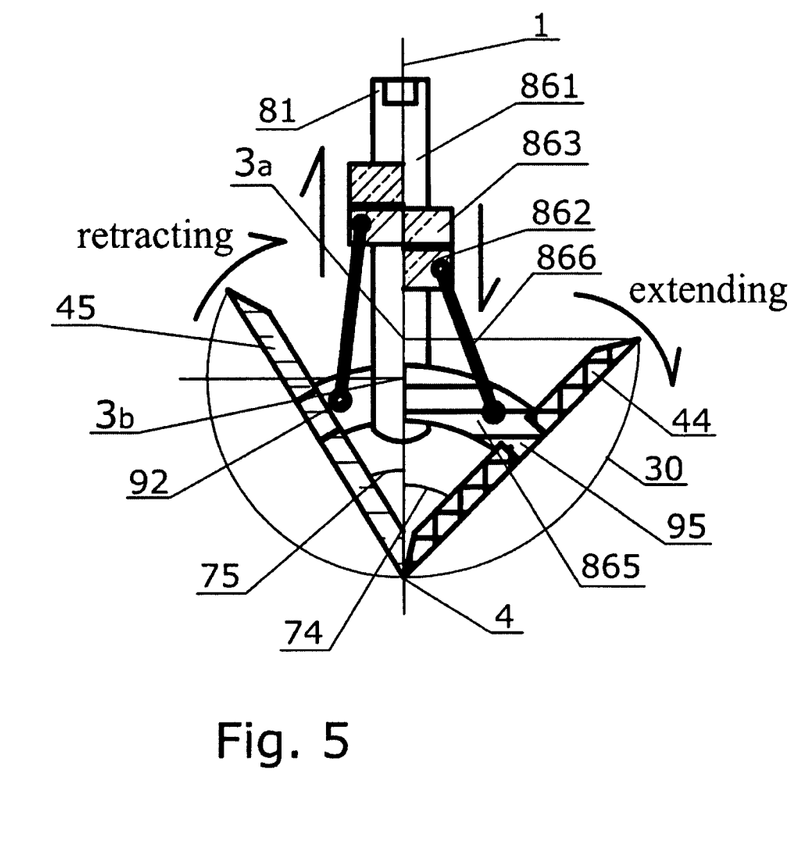
FIG. 5 is a cross-sectional view of an example of the reamer assembly fabricated with an adjustable mechanism for regulating the cutting profile of the reamer during operation called "all in one" design. Left and right portion of the figure have shown a reamer assembly in the retracting and the extending position, respectively.

As illustrated in FIG. 5, a fourth preferred embodiment describes a design of the reamer assembly with the "all in one piece" design. The reamer assembly possesses two identical sized and shaped cutting elements, such as circular cutting blades (44 shown at the extending position and 45 shown at the retracting position, respectively) symmetrically assembled around the primary axis 1 and a featured frame particularly equipped with actuating mechanism, which gives surgeons ability to adjust a cutting profile of the reamer assembly by fine tuning independent factor(s) or parameter(s) in order to ream any particular size of cavity.

The featured frame comprises of a base component 861, a sliding-able lower 862 and upper sleeve 863, a pair of swing-able facet site 865 and a pair of the link legs 866.

The base component 861 has an elongated, cylindrical shape with an engagement port 81 at upper end thereof for coupling with the rotary shaft 20 as described previously, a middle portion and a distal portion, respectively. The distal portion constructs a tunnel like, arc-shaped trough that has a track radius, $r_{track}$ and arc about 10 to 60 degrees with a center at the apex point 4 of the reamer assembly. The arc-shaped trough forms an orbit for curbing the motion of the pair of swing-able facet sites 865 around the apex point 4.

A major portion of the swing-able facet site 865 is configured by an arc-shaped rib or rod with a feature which could be precisely fit into the arc-shaped trough on the base component. Two swing-able facet sites 865 may swing in the track of the trough to be toward or away from the primary axis 1 around the apex point 4. A swinging angle, $\phi$ 74 (as shown at extending position) or 75 (as shown at the retracting position) is defined as the angle between the plane of the cutting element (circular cutting blade) and an extension line of the primary axis 1 and follows formula (3).

$$\sin(180-\phi) = r_{CE}/R_{sph} \quad (3).$$

Formulas (1) and (2) are still valid for determining parameters of the reamer assembly and dimension of the sphere reamed. The relationship between $\phi$ and $\alpha$ defines: $\phi = \alpha - 90$.

There are spindles 95 extending from the exterior end of each rib for coupling with the specific circular cutting blade. Axis of the spindle 95 is coaxially oriented with the secondary axis. There is a pivotal pin 92 between the structures of rib and spindle 95 on each facet site 865 for the link leg 866 to pivotally connect the lower sleeve 862 and the swingable facet site 865 together. Two swing-able facet sites 865 have mirror symmetrical structure to each other and are symmetrically assembled in face to face manner into the arc-shaped trough, which engages the swingable facet sites 865 in extending or retracting on the track of the arc-shaped trough with a respect to the apex point 4 of the reamer assembly as a swing center.

The sliding-able sleeves 862 and 863 are free sliding on the middle portion of the base component 861 along the longitude direction of the primary axis 1 together and join together with a bearing structure allowing that the upper sleeve 863 is free from the spinning of both the driving shaft and the lower sleeve 862. The lower sleeve 862 has two separate pivot sites located on the side of the sleeve with 180 degree angle apart, which configures a site for the link legs 866. The upper sleeve 863 is equipped with a mechanism for coupling with the adjustment handle, or like, for extending (shown as the right side of the FIG. 5) or retracting (shown as the left side of the FIG. 5) the facet sites, enabling the regulation of the cutting profile of the reamer assembly without interference with the rotation of the rotating shaft or the featured frame.

Each link leg 866 pivotally connects the lower sleeve 862 and the specific facet site together. Two circular cutting blades have been assembled on the specific spindle 95 of the facet site 865 and form a V-shaped static profile. The lower points on the cutting edge of two circular cutting blades are always immediately adjacent to each other and locates at the apex point 4, in spite of adjustment of parameter φ 74 or 75. The radius of the cutting blade used should follow the relationship in accordance of formula (4) below or be larger than the calculated value from formula (4):

$$r_{CE} = 0.707 \times R_{large} \quad (4)$$

where $R_{large}$ is a radius of the largest hemisphere sought to be cut.

The actuating mechanism generally provides translational movement, utilizing a number of translating mechanisms: the adjustment handle conducts linear motion to the upper/lower sleeve 863 and 862, the lower sleeve 862 converts the linear motion to the swinging motion of the pair of facet sites 865 through the pair of link legs 866 and varying the swing angle φ. As well known, along with the variation of the φ, the virtual center of the reamer assembly also is shifted as $3_a$, corresponding to φ 74 and $3_b$ corresponding to φ 75 as well.

Figure 6:
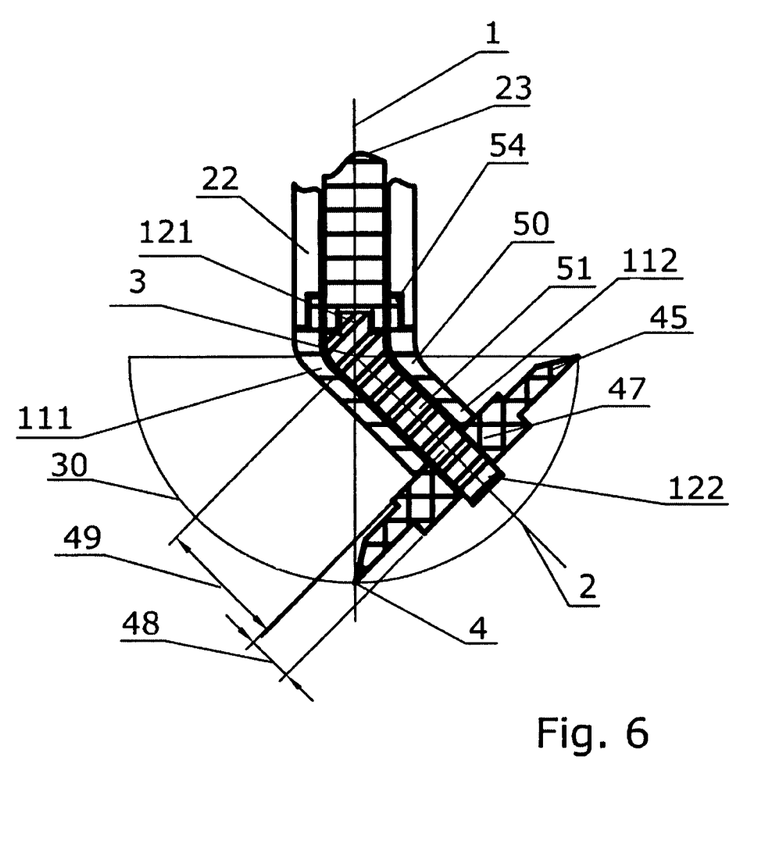
FIG. 6 is a cross-sectional view of another example of the reamer assembly with the interchangeable circular cutting blade affiliated with the cutting mechanism of active, two axis rotations of cutting.

Referring to FIG. 6, a fifth preferred embodiment describes that the reamer assembly particularly has at least one interchangeable, circular cutting blade 45, which may be directly powered by auxiliary shaft 23 and actively spin on secondary axis 2, defined as first order cutting, whilst the featured frame 50 powered by main shaft 22 motivates the cutting blade 45 to revolve on this circular orbit around the primary axis 1, defined as secondary order cutting.

The reamer assembly comprises of a curved tubular featured frame 50, an angled shaft 51 and an interchangeable, circular cutting blade 45.

The featured frame 50 possesses an exterior feature 54 on its top end for coupling with the main shaft 22 and a curved shaft tunnel allowed the angled shaft 51, a soft shaft, or something like with the same functions, to be inserted through. The shaft tunnel possesses two end openings, upper 111 and lower exit 112, respectively. There is a virtual center 3 of featured frame 50 defined on the middle of the tunnel, which corresponds to the center of the sphere 30 as described in other embodiments previously. The upper 111 and lower exit 112 of the tunnel has an own axis which is consistent with the primary axis 1 and the secondary axis 2, respectively. The angle of the curved tunnel here, is approximately 135 degree between two axis of the ends, or like.

The angled shaft 51, or like, has been curved with approximately 135 degree angle between two of the end axis thereof and possesses an adaptor on each end thereof, called as the upper adaptor 121 and lower adaptor 122, respectively. Each adaptor has an exterior configuration for matching and pairing with a formation on the corresponding exit 111 and 112 of the tunnel, respectively, which allows the angled shaft to freely spin in the tunnel when it is assembled within the featured frame 50. The upper adaptor 121 possesses a structure to be able to pair with the auxiliary shaft 23. The lower adaptor 122 has a feature to allow coupling with a featured coupler 47 of the cutting blade 45.

The cutting blade 45 has a predetermined radius $r_{CE}$ and the coupler 47 with a varied length along the longitude direction of the primary axis: $\Delta_{orb}$, 48 defined by $\Delta r_{orb} = r_{orb} - r_{att}$. The coupler 47 has a structure on its center to affix with the feature on the lower adaptor 122 of the angled shaft 51. A distal end of the coupler 47 is paired with the circular cutting blade 45. So the circular cutting blade 45 is able to actively spin on its secondary axis, whilst revolving on its orbit around the primary axis 1. The orbit here is defined by $r_{orb}$ and $r_{CE}$. The $r_{att}$ 49 is equivalent to an effective distance from virtual center 3 to the contact facet on the lower adaptor 122 of the angled shaft 51 with the coupler 47.

In this particular design, the feature parameters of each reamer assembly: $r_{orb}$ and $r_{CE}$ are variable factors. In order to satisfy different size of the sphere sought to be reamed, there is a series of the interchangeable cutting blade 45 with a predetermined radius, $r_{CE}$ and a corresponding length, $\Delta r_{orb}$ 48 of the coupler 47. During the operation, the cutting blade powered by auxiliary shaft 23 actively spins at higher turning speed on the secondary axis 2 and uniformly cut every point met on the surface, whilst the featured frame 50 powered by main shaft 22 and drives the cutting blade to revolve on the orbit around the primary axis at a regular turning speed. The dual, active motion (two axis rotation) of the cutting blade could generate a perfect hemispherical concave on any object, because there is no dead point on any position of the spherical surface to be cut at all. It overcomes a drawback of that the rotation in one dimension always has a dead point on its rotating center regarding zero rotary speed thereon.

While this invention has been described as having few preferred designs, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What we claim:
1. A device for shaping a spherical surface comprising:
   a drive shaft rotating about a longitudinal axis;
   at least one attachment frame having at least two mounting sites referenced to a common spherical center located on the longitudinal axis;
   each mounting site having a corresponding circular cutting element with cutting edge at its circumference;

each corresponding cutting element having its own self-spinning axis intersecting the longitudinal axis at the common spherical center, and a cutting depth, D, along the longitudinal axis;

the cutting edge circumference of all the corresponding cutting elements maintains a common distance defining a common spherical radius, $R_{sph}$, referenced to the common spherical center;

at least one of the corresponding cutting elements having a different cutting depth from at least one other corresponding cutting element; and an overall cutting depth of the spherical surface to be shaped by the device is determined by a permutation of all the cutting depths of all the corresponding cutting elements along the longitudinal axis; wherein common spherical radius, $R_{sph}$, is determined by selecting a proper combination of an arm length, $r_{orb}$, of the attachment frame, and the cutting element radius, $r_{ce}$, of each cutting element; and the cutting depth of each corresponding cutting element is determined by a proper combination of the cutting element radius, $r_{ce}$, and a tilt angle, $\alpha$, of each cutting element, according to the following expressions, respectively:

$$R_{sph} = \sqrt{(r_{orb})^2 + (r_{ce})^2}; \quad 1)$$

and $$D = 2 r_{ce} \sin(180 - \alpha). \quad 2)$$

2. The device of claim 1, wherein
at least one of the corresponding cutting element cutting edge intersects the longitudinal axis at the common distance; wherein
the cutting depth of at least one of the corresponding cutting element is partially overlapped with the cutting depth of another cutting element.

3. The device of claim 1, wherein the attachment frame further comprises:
a first attachment frame and a second attachment frame concentrically arranged;
each of the first attachment frame and the second attachment frame having at least two mounting sites arranged symmetrically apart from the longitudinal axis; wherein
the first attachment frame and the second attachment frame are independently driven by the drive shaft.

4. The device of claim 3, wherein
the drive shaft has a main drive shaft and an auxiliary drive shaft concentrically arranged;
the first attachment frame is driven at a lower rotating speed by the main drive shaft; and
second attachment frame is driven at a higher rotating speed by the auxiliary drive shaft concentrically resided within the main drive shaft.

5. The device of claim 3, wherein
the corresponding cutting elements of the first attachment frame having different cutting depth from the corresponding cutting elements of the second attachment frame; and
the cutting depths of the corresponding cutting elements of the first and second attachment frames, respectively, are adjacent to each other.

6. The device of claim 3, wherein
the corresponding cutting elements of the first attachment frame and the second attachment frame having different tilt angles, respectively; and the cutting depths of the corresponding cutting elements of the first and second attachment frames, respectively, are adjacent to each other.

7. The device of claim 6, wherein
the first attachment frame is driven at a first rotating speed;
the second attachment frame is driven at a second rotating speed.

8. The device of claim 1, wherein
the arm length, $r_{orb}$, of each mounting site, and the cutting element radius, $r_{ce}$, of each corresponding cutting element, are the same; and
the cutting edge of one of the corresponding cutting element intersects the longitudinal axis at the common distance.

9. The device of claim 8, wherein
the tilt angles of the at least two mounting sites, respectively, are different from each other; and
the cutting depths of the corresponding cutting element of the at least two mounting sites, respectively, are partially overlapped to each other.

10. A device having an adjustable cutting profile for shaping at least a portion of a spherical surface comprising:
an attachment base having at least one guiding slot and rotating around a longitudinal axis;
an adjustment mechanism located on the attachment base;
a plurality of arms, each being moveable within the corresponding guiding slot, having mounting site connected to a circular cutting element at a distal end; and
a plurality of links connected to each corresponding arms to the adjustment mechanism; wherein
each cutting element having a cutting surface rotating around its own self-spinning axis, a radius, $r_{ce}$, a tilt angle, $\alpha$, defining an angle between the longitudinal axis and the self-spinning axis, a cutting depth, D, of a partial spherical surface to be shaped, an arm length, $r_{orb}$, defining a distance between a common spherical center along the longitudinal axis and a circular center of the cutting surface, and forming a spherical radius, $R_{sph}$, of a partial spherical surface to be shaped; wherein
the spherical radius, $R_{sph}$, is determined by selecting the proper combination of the arm length, $r_{orb}$, and the cutting element radius, $r_{ce}$, of each cutting element; and
the cutting depth, D, of the partial spherical surface shaped is determined by selecting the proper combination of the cutting element radius, $r_{ce}$, and the tilt angle, $\alpha$, of each cutting element, according to the following expressions, respectively:

$$R_{sph} = \sqrt{(r_{orb})^2 (r_{ce})^2}; \quad 1)$$

and $$D = 2 r_{ce} \sin(180 + \alpha); \quad 2)$$

wherein
the portion of the spherical surface to be shaped by the device is a permutation of all the partial spherical surfaces shaped by each cutting element along a direction of the longitudinal axis.

11. The device of claim 10, wherein
varying the spherical radius, $R_{sph}$, is equivalent to varying the arm length, $r_{orb}$, of the corresponding cutting element according to the formula 1).

12. The device of claim 10, wherein
each cutting element mounted on the corresponding arms is referenced to the same common spherical center, forming the same spherical radius, $R_{sph}$; wherein the cutting depth, D, of each of the cutting element is arranged to be partially overlapped, completely overlapped or adjacent with each other.

13. The device of claim 12, wherein
the guiding slot is arc-shaped, having a track radius, $r_{rack}$, and a track center thereof situated at an imaginary apex of the spherical surface to be shaped by the device.

14. The device of claim 13, wherein
the plurality of arms comprising a pair of arc-shaped swing arms movable within the arc-shaped guiding slot;
each of the swing arms has a swing angle, $\phi$, defined by an angle between a horizontal plane of each cutting element and the longitudinal axis;
the adjustment mechanism continually varying the swing angle, $\phi$, by moving the swing arms through the guiding slot referenced to the track center.

15. The device of claim 14, wherein
the varying of the swing angle, $\phi$, is equivalent to simultaneously varying both the spherical radius, $R_{sph}$, and the cutting depth, D, of the cutting element.

16. The device of claim 14, wherein
the adjustment mechanism having sliding members coupled with each of the corresponding plurality of links for continually varying at least the spherical radius, $R_{sph}$, of each cutting element.

17. A device having a variable cutting profile for shaping a spherical surface comprising:
a hollow main drive shaft rotating about a longitudinal axis;
an auxiliary drive shaft concentrically arranged within the main drive shaft;
an attachment frame driven by the main drive shaft, having an angled passage with a predetermined tilt angle, $\alpha$;
the angled passage has a frame length, $r_{att}$, spaced away from a common spherical center of the spherical surface to be shaped on the longitudinal axis;
an one-piece angled soft shaft arranged within the angled passage, driven directly by the auxiliary drive shaft at one end;
an interchangeable circular cutting element with cutting edge at its circumference;
the cutting element having its own self-spinning axis referenced to the common spherical center;

the cutting edge circumference of the cutting element maintains a common distance defining a spherical radius, $R_{sph}$, of the spherical surface to be shaped, referenced to the common spherical center;
the cutting edge of the cutting element intersects the longitudinal axis at the common distance;
the cutting element having an integral coupler with a specific coupler length, $\Delta r_{orb}$, and a predetermined radius, $r_{ce}$; and
the integral coupler is connected to another end of the angled soft shaft;
the cutting edge of the cutting element maintains a common distance defining the spherical radius, $R_{sph}$, referenced to the common spherical center; wherein
a total arm length, $r_{orb}$, of the cutting element is determined by:

$$r_{orb} = r_{att} + \Delta r_{orb};$$

the cutting element has a cutting depth, D, determined by an angle combination of the tilt angle, $\alpha$, and the radius, $r_{ce}$, according to a formula:

$$D = 2 r_{ce} \sin(180 - \alpha), \quad\quad\quad 1)$$

and
the common spherical radius, $R_{sph}$, of the spherical surface to be shaped is determined by a combination of the radius, $r_{ce}$, and the total arm length, $r_{orb}$, of the corresponding cutting element, according to a formula:

$$R_{sph} = \sqrt{(r_{orb})^2 + (r_{ce})^2}. \quad\quad\quad 2)$$

18. The device of claim 17, wherein
the cutting element is interchangeable with another cutting element having different cutting element radius and coupler length.

19. The device of claim 17, wherein
the main drive shaft is rotating at a lower speed than the auxiliary drive shaft; and
the spherical radius, $R_{sph}$, of the spherical surface to be shaped is variable by the arm length, $r_{orb}$, according to formula 2).

* * * * *